United States Patent
Zeller et al.

(10) Patent No.: US 8,366,318 B2
(45) Date of Patent: Feb. 5, 2013

(54) INTRAORAL X-RAY SENSOR WITH EMBEDDED STANDARD COMPUTER INTERFACE

(75) Inventors: Uwe Zeller, Biberach (DE); Doug Golay, Coon Rapids, IA (US)

(73) Assignee: Dental Imaging Technologies Corporation, Hatfield, PA (US)

( * ) Notice: Subject to any disclaimer, the term of this patent is extended or adjusted under 35 U.S.C. 154(b) by 318 days.

(21) Appl. No.: 12/796,251

(22) Filed: Jun. 8, 2010

(65) Prior Publication Data
US 2011/0013745 A1    Jan. 20, 2011

Related U.S. Application Data

(60) Provisional application No. 61/226,556, filed on Jul. 17, 2009.

(51) Int. Cl.
  *A61B 6/14*    (2006.01)
(52) U.S. Cl. ......................................... 378/169; 378/168
(58) Field of Classification Search ................. 378/98.8, 378/168, 169, 191; 250/370.09, 370.15
  See application file for complete search history.

(56) References Cited

U.S. PATENT DOCUMENTS

| | | | |
|---|---|---|---|
| 4,057,732 A | 11/1977 | Klauser | |
| 4,259,583 A | 3/1981 | Albert | |
| 4,593,400 A | 6/1986 | Mouyen | |
| 4,866,750 A | 9/1989 | Chavarria et al. | |
| 5,331,166 A | 7/1994 | Crosetto et al. | |
| 5,434,418 A | 7/1995 | Schick | |
| 5,471,515 A | 11/1995 | Fossum et al. | |
| 5,510,623 A | 4/1996 | Sayag et al. | |
| 5,513,252 A | 4/1996 | Blaschka et al. | |
| 5,514,873 A | 5/1996 | Schulze-Ganzlin et al. | |
| 5,519,751 A | 5/1996 | Yamamoto et al. | |
| 5,574,250 A | 11/1996 | Hardie et al. | |
| 5,677,537 A | 10/1997 | Pfeiffer | |
| 5,691,539 A | 11/1997 | Pfeiffer | |
| 5,694,448 A | 12/1997 | Morcom | |
| 5,757,011 A | 5/1998 | Whitebook et al. | |
| 5,784,429 A | 7/1998 | Arai | |
| 5,789,711 A * | 8/1998 | Gaeris et al. .............. 174/131 A |
| 5,887,049 A | 3/1999 | Fossum | |

(Continued)

FOREIGN PATENT DOCUMENTS

| | | |
|---|---|---|
| DE | 19815637 | 10/1998 |
| EP | 0415075 | 3/1991 |

(Continued)

OTHER PUBLICATIONS

Nixon, R.H., et al., "128X128 CMOS Photodiode-Type Active Pixel Sensor with On-Chip Timing, Control and Signal Chain Electronics", SPIE, vol. 2415, pp. 117-123, 1995.

(Continued)

*Primary Examiner* — Glen Kao
(74) *Attorney, Agent, or Firm* — Michael Best & Friedrich LLP

(57) ABSTRACT

An intraoral x-ray sensor with embedded standard computer interface. The sensor includes a data transfer cable with improved mechanical strength and heat transferring properties. The cable is quad-twisted USB cable and includes two data lines, a ground line, and fillers twisted within a metallic sheath, e.g., a metal braided shield. The cable is symmetrically organized about a centerline. The symmetric cable has an improved life due to the ability to withstand mechanical stress (e.g., rotational stress). The sensor includes a processor and a housing with an inner metallization layer. The sheath is coupled to the inner metallization layer to transfer heat generated by the processor from the inner metallization layer to the sheath.

18 Claims, 8 Drawing Sheets

DIRECTION OF X-RAY RADIATION

U.S. PATENT DOCUMENTS

| | | | |
|---|---|---|---|
| 5,894,129 A | 4/1999 | Pool | |
| 5,912,942 A | 6/1999 | Schick et al. | |
| 6,002,742 A | 12/1999 | Nelvig | |
| 6,011,251 A | 1/2000 | Dierickx et al. | |
| 6,030,119 A | 2/2000 | Tachibana et al. | |
| 6,033,111 A | 3/2000 | Winters et al. | |
| 6,042,267 A | 3/2000 | Muraki et al. | |
| 6,069,935 A | 5/2000 | Schick et al. | |
| 6,074,503 A * | 6/2000 | Clark et al. | 174/131 A |
| 6,134,298 A | 10/2000 | Schick et al. | |
| 6,169,781 B1 | 1/2001 | Doebert et al. | |
| 6,203,195 B1 | 3/2001 | Willis | |
| 6,244,866 B1 | 6/2001 | Campbell | |
| 6,307,915 B1 | 10/2001 | Frojdh | |
| 6,320,934 B1 | 11/2001 | Carroll et al. | |
| 6,343,875 B1 | 2/2002 | Eppinger et al. | |
| 6,404,854 B1 | 6/2002 | Carroll et al. | |
| 6,462,268 B1 | 10/2002 | Hazy et al. | |
| 6,527,442 B2 | 3/2003 | Carroll | |
| 6,652,141 B1 | 11/2003 | Cianciosi | |
| 6,744,068 B2 | 6/2004 | Fossum et al. | |
| 6,797,960 B1 | 9/2004 | Spartiotis et al. | |
| 6,811,312 B2 | 11/2004 | Bratslavsky et al. | |
| 6,833,548 B2 | 12/2004 | Homme et al. | |
| 6,898,268 B2 | 5/2005 | Makila et al. | |
| 6,919,569 B2 | 7/2005 | Homme et al. | |
| 6,924,486 B2 | 8/2005 | Schick et al. | |
| 6,932,505 B2 | 8/2005 | Yao et al. | |
| 6,972,411 B2 | 12/2005 | Schick et al. | |
| 6,974,253 B2 | 12/2005 | Ihalainen | |
| 7,006,600 B1 | 2/2006 | Krema et al. | |
| 7,016,466 B2 | 3/2006 | Rinaldi et al. | |
| 7,033,075 B2 | 4/2006 | Landis et al. | |
| 7,036,985 B2 | 5/2006 | Puente et al. | |
| 7,072,443 B2 | 7/2006 | Schick et al. | |
| 7,090,395 B2 | 8/2006 | Glazer | |
| 7,091,465 B2 | 8/2006 | Miyaguchi | |
| 7,172,339 B2 | 2/2007 | Diederich | |
| 7,193,219 B2 | 3/2007 | Schick et al. | |
| 7,195,395 B2 | 3/2007 | Quarry et al. | |
| 7,210,847 B2 | 5/2007 | Hack | |
| 7,281,847 B2 | 10/2007 | Kokkaliaris et al. | |
| 7,360,948 B2 | 4/2008 | Razzano et al. | |
| 7,425,095 B2 | 9/2008 | Schmulenson et al. | |
| 7,462,807 B2 | 12/2008 | Caupain et al. | |
| 7,563,026 B2 | 7/2009 | Mandelkern et al. | |
| 7,608,834 B2 | 10/2009 | Boucly et al. | |
| 7,659,516 B2 | 2/2010 | Korthout et al. | |
| 7,711,173 B2 | 5/2010 | Inglese | |
| 2004/0188625 A1 | 9/2004 | Schulze-Ganzlin | |
| 2006/0257816 A1 | 11/2006 | Klemola et al. | |
| 2006/0262461 A1 | 11/2006 | Wood | |
| 2007/0147675 A1 | 6/2007 | Ulrici et al. | |
| 2007/0176109 A1 | 8/2007 | Bell | |
| 2007/0286335 A1 | 12/2007 | De Godzinsky | |
| 2008/0095321 A1 | 4/2008 | Calderwood et al. | |
| 2008/0118028 A1 | 5/2008 | Stantchev | |

FOREIGN PATENT DOCUMENTS

| | | |
|---|---|---|
| EP | 1230896 | 8/2002 |
| EP | 1252762 | 10/2002 |
| EP | 1255401 | 11/2002 |
| EP | 1378201 | 1/2004 |
| EP | 1623673 | 2/2006 |
| EP | 1746442 | 1/2007 |
| EP | 1803400 | 7/2007 |
| GB | 1514851 | 6/1978 |
| JP | 08-000603 | 1/1996 |
| WO | 92/22188 | 12/1992 |
| WO | 96/32064 | 10/1996 |
| WO | 01/58148 | 8/2001 |
| WO | 02/063338 | 8/2002 |
| WO | 03/032839 | 4/2003 |
| WO | 2006/004528 | 1/2006 |
| WO | 2006/008339 | 1/2006 |
| WO | 2006/034978 | 4/2006 |
| WO | 2006/089003 | 8/2006 |
| WO | 2006/093869 | 9/2006 |
| WO | 2006/103126 | 10/2006 |
| WO | 2007/003495 | 1/2007 |
| WO | 2007/022246 | 2/2007 |
| WO | 2007/030381 | 3/2007 |
| WO | 2007/044412 | 4/2007 |
| WO | 2007/142925 | 12/2007 |
| WO | 2008/058865 | 5/2008 |
| WO | 2008/103460 | 8/2008 |
| WO | 2009/055136 | 4/2009 |
| WO | 2009/058467 | 5/2009 |
| WO | 2009/058468 | 5/2009 |

OTHER PUBLICATIONS

Mendis, S.K., et al., "A 128X128 CMOS Active Pixel Image Sensor for Highly Integrated Imaging Systems", IEEE IEDM Technical Digest, pp. 583-586, 1993.

Andoh, F., et al., "A 250,000-Pixel Image Sensor with FET Amplification at Each Pixel for High-Speed Television Cameras", IEEE ISSCC Digest of Technical Papers, pp. 212-213, Feb. 1990.

Fossum, Eric, R., "CMOS Image Sensors: Electronic Camera-On-A-Chip", IEEE Transactions on Electron Devices, vol. 44, No. 10, pp. 1689-1698, Oct. 1997.

Universal Serial Bus Specification, Chapter 6—Mechanical, Revision 2.0, Apr. 27, 2000.

Spartiotis, Konstantinos, et al., "A Directly Converting High-Resolution Intra-Oral X-Ray Imaging Sensor", Nuclear Instruments and Methods in Physics Research, Section A, 501, pp. 594-601, Elsevier Science B.V., 2003.

Hong, Soonil, et al, "Development and Evaluation of a CMOS Sensor-Based Digital Intra-Oral Radiographic System", IEEE Transactions on Nuclear Science, vol. 52, No. 1, Feb. 2005.

International Search Report and Written Opinion, International Application No. PCT/US2010/039322, mailed Aug. 17, 2010.

International Search Report and Written Opinion, International Application No. PCT/US2010/039324, mailed Oct. 8, 2010.

* cited by examiner

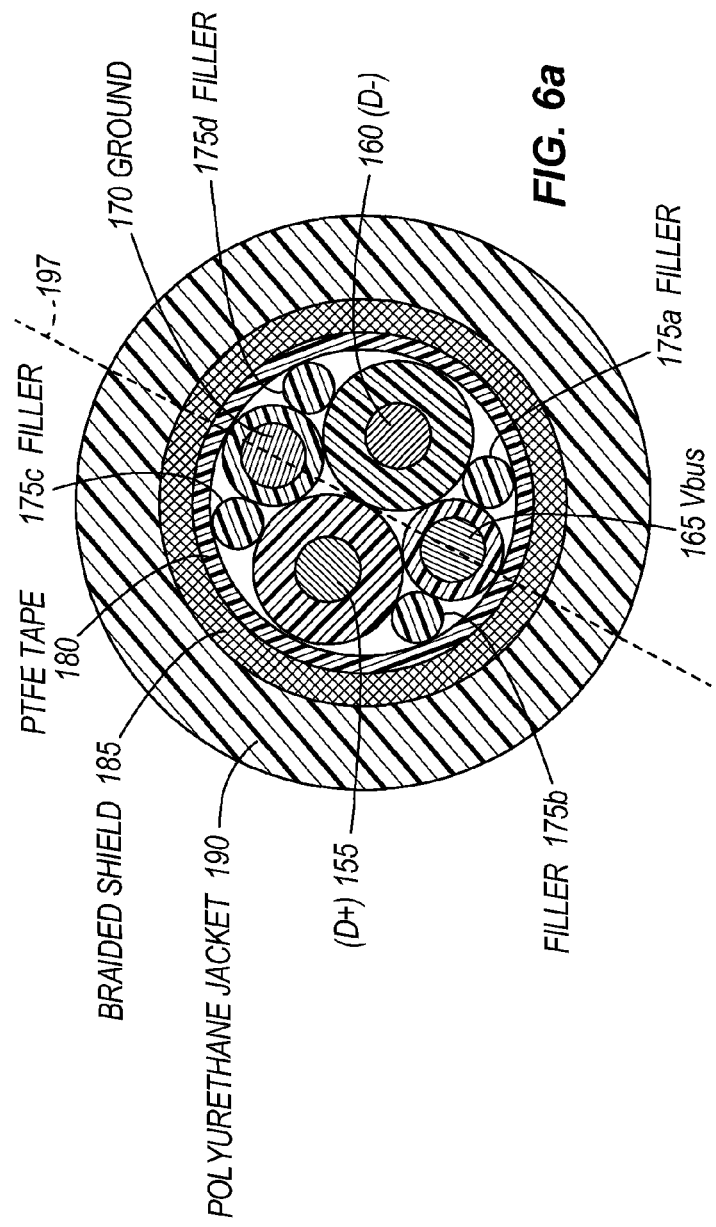
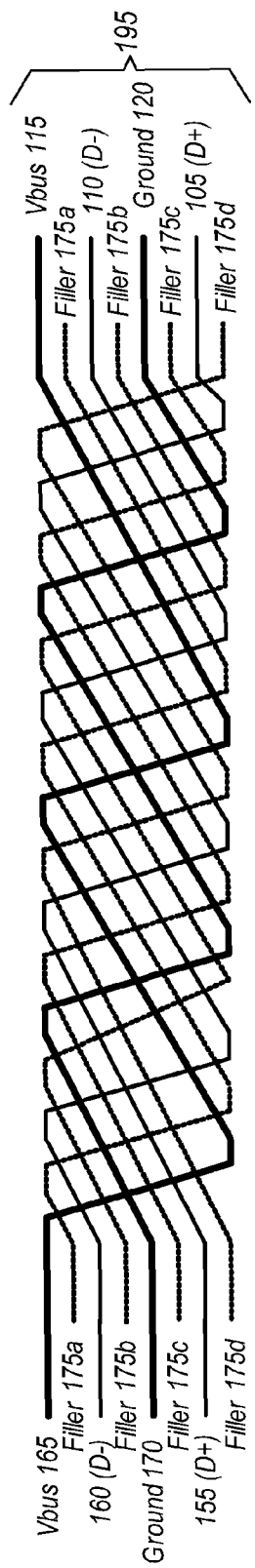
FIG. 6a
FIG. 6b

INTRAORAL X-RAY SENSOR WITH EMBEDDED STANDARD COMPUTER INTERFACE

CROSS-REFERENCE TO RELATED APPLICATIONS

The present application claims priority to U.S. Provisional Patent Application Ser. No. 61/226,556, filed Jul. 17, 2009, the entire contents of which is hereby incorporated by reference. This application is also related to U.S. patent application Ser. No. 12/605,624, filed Oct. 26, 2009, U.S. Provisional Patent Application Ser. No. 61/108,552, filed Oct. 27, 2008, and U.S. Provisional Patent Application Ser. No. 61/226,533, filed Jul. 17, 2009, the entire contents of which are hereby incorporated by reference.

BACKGROUND

The present invention relates to x-ray imaging, including dental x-ray imaging. More particularly, embodiments of the invention relate to a data transfer cable for an intraoral sensor with improved mechanical strength and heat transfer properties X-rays have been used in dentistry to image teeth and parts of the mouth for many years. In general, the process involves generating x-rays and directing the x-rays at the patient's mouth. The x-rays are attenuated differently by different parts of the mouth (e.g., bone versus tissue) and this difference in attenuation is used to create an image, such as on film or by using electronic image sensor.

SUMMARY

One challenge associated with electronic intraoral x-ray systems relates to the mechanical stress on a cable coupling the sensor capturing images and an output device, such as a computer. To capture dental x-ray images, the intraoral sensor is positioned within the oral cavity of each patient, which often includes twisting and tugging forces being exerted on the cable. The repeated and continuous positioning of the intraoral sensor for each patient results in increased mechanical stress, which wears the cable. With increased use and wear, the cable can malfunction and become unusable.

An additional challenge relates to the environment in which the intraoral sensor operates: the oral cavity of a patient. The electronics within the intraoral sensor generate heat and, if left unchecked, can result in injury to the patient. Certain governmental regulations or other standards apply to devices, such as intraoral sensors, that limit the maximum operating temperature. For instance, safety standard 60601-1 $2^{nd}$ edition from the International Electrotechnical Commission (IEC) limits the outside temperature of such intraoral sensors to 41 degrees Celsius.

Embodiments of the invention provide, among other things, an intraoral sensor including a sensor housing having a top portion and a bottom portion. The sensor further includes a twisted-quad universal serial bus (USB) cable coupled to the top portion. The twisted-quad USB cable includes an outer sheath and, within the outer sheath, a first data line, a second data line, a ground line, a power line, and four fillers that are twisted together to form a single bundle. The sensor also includes circuitry within the sensor housing. The circuitry converts x-rays received through the bottom portion into x-ray data and outputs the x-ray data along the twisted-quad USB cable.

In some embodiments, the first data line, the second data line, the ground line, the power line, and the four fillers are symmetrically organized about a centerline of the twisted-quad USB cable. Additionally, in some embodiments, the four fillers includes a first filler, a second filler, a third filler, and a fourth filler. The first filler abuts the ground line and the first data line; the second filler abuts the ground line and the second data line; the third filler abuts the power line and the first data line; and the fourth filler abuts the power line and the second data line. In some embodiments, the four fillers are made of a plastic, electrically insulating material.

In some embodiments, the outer sheath includes a braided shield and is coupled via a heat-conducting wire to a metallic layer substantially covering an inner surface of the top portion. In some embodiments, the outer sheath further comprises a jacket layer outside of the braided shield and a tape layer inside of the braided shield. Additionally, in some embodiments, the sensor includes an isolation layer within the sensor housing. The isolation layer is between the circuitry and the top portion and wherein the isolation layer is electrically insulating and heat conducting. In some embodiments, the isolation layer is coupled to one of the metallic layer and the braided shield via one of a second heat-conducting wire and direct contact to provide heat transfer from within the sensor housing to the twisted-quad USB cable.

Additionally, embodiments of the invention provide an intraoral x-ray sensor including a housing and circuitry within the housing. The housing includes a top portion and a bottom portion. The top portion has a first inner surface and a first thermal resistance. The first inner surface is substantially covered by a metallic layer with a second thermal resistance that is lower than the first thermal resistance. The circuitry converts x-rays received through the bottom portion into x-ray data and outputs the x-ray data along a data cable. The data cable includes wires within a metallic shield. The metallic shield is coupled to the metallic layer by a thermally conductive path that has a thermal resistance that is less than the thermal resistance of air.

In some embodiments, the bottom portion includes a second inner surface substantially covered by a second metallic layer that is coupled to the metallic layer either directly or via another thermally conductive path. The circuitry is contained on a printed circuit board (PCB) that is isolated from the metallic layer by an isolation layer. The isolation layer is thermally conductive and electrically insulating, and includes (in some implementations) an opening through which the circuitry and the wires are connected. Additionally, in some embodiments, the circuitry includes an array of pixels on a first side of the PCB and, on a second side of the PCB, a processor and an input/output module. The sensor includes x-ray attenuation components between the second side and a surface of the bottom portion through which x-rays are received. The x-ray attenuation components may include: a lead layer, a fiber optic covered by a scintillating layer, and copper planes. The top portion includes a dome (with the shape of a partial, elliptical paraboloid) having a face with a circular opening. The circular opening receives the data cable.

Other aspects of the invention will become apparent by consideration of the detailed description and accompanying drawings.

BRIEF DESCRIPTION OF THE DRAWINGS

FIG. 6a depicts a cross section of a cable according to embodiments of the invention.

FIG. 6b depicts a wiring diagram of a cable according to embodiments of the invention.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
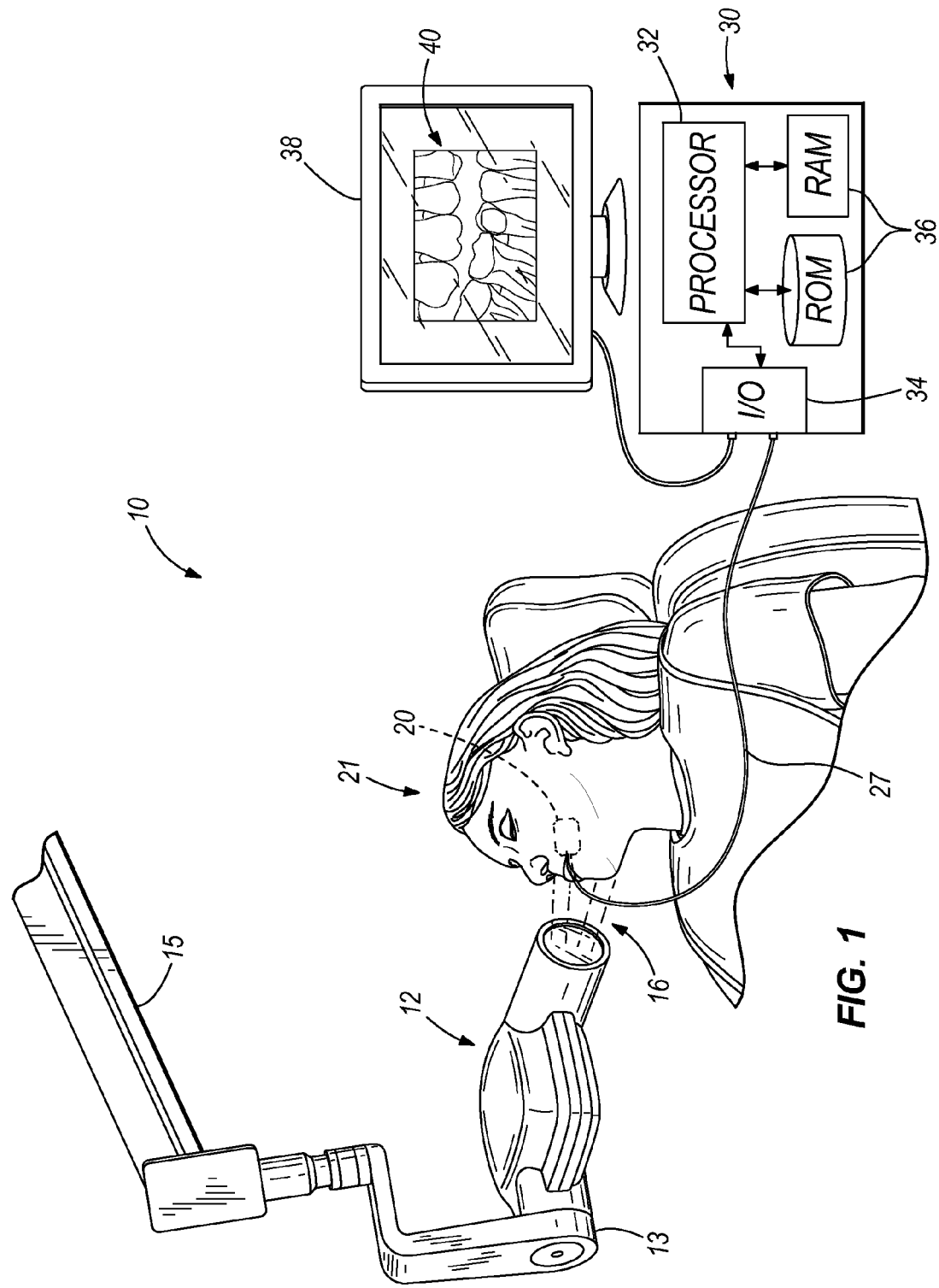
FIG. 1 is a schematic illustration of a dental x-ray system including an x-ray source, an intraoral sensor located in a patient's mouth, and a computer connected to the intraoral sensor.

FIG. 1 illustrates a dental x-ray system 10. The system includes an x-ray source 12. In the embodiment shown, the source is located on an end 13 of a mechanical arm 15. When activated, the x-ray source 12 generates an x-ray stream 16 that has a generally circular cross-section. (Of course, x-rays are generally invisible, but a representation of a stream is illustrated to facilitate understanding of the invention.) In many applications, a collimator is used to reduce the size of the stream and generate a smaller x-ray stream having a rectangular cross-section. A collimator may be used with a mechanical positioning device to help align the x-ray stream with an x-ray sensor. As shown in FIG. 1, x-ray source 12 is positioned (e.g., by an operator) so that the x-ray stream 16 is directed to an intraoral sensor 20. The intraoral sensor 20 is shown located in the mouth of a patient 21. In some embodiments, the intraoral sensor 20 includes a scintillator that coverts x-ray radiation to visible light. In other embodiments, the sensor 20 is configured to convert x-rays into electric charge without a scintillator. Unless otherwise specified, the term pixel refers both to a pixel in the array of pixels that converts x-rays to electrons without a scintillator and a pixel in the array of pixels and its associated scintillator or portion of a scintillator.

Figure 1A:
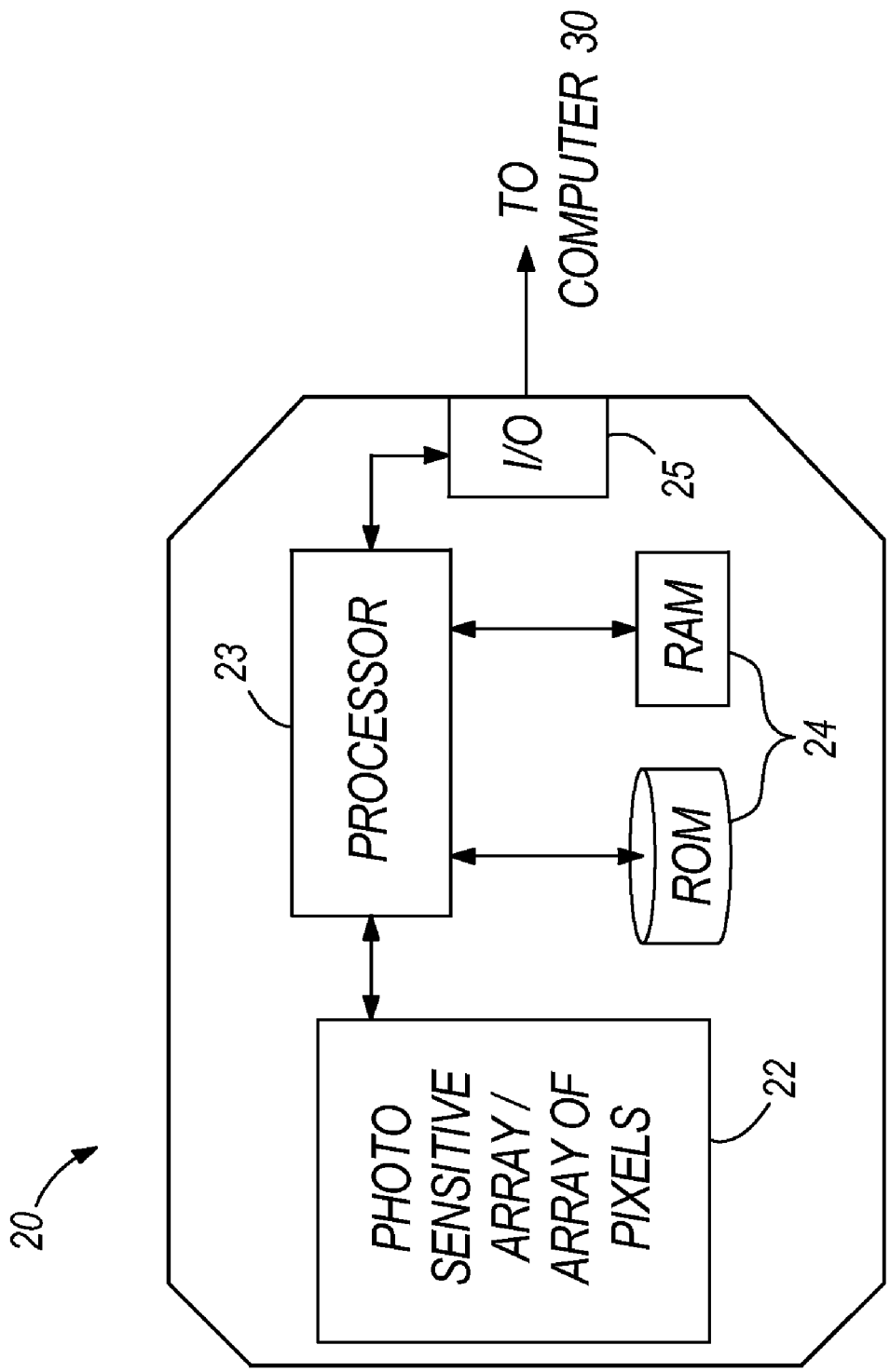
FIG. 1a is a schematic illustration of the intraoral sensor shown in FIG. 1 showing internal components of the sensor.

As best seen by reference to FIG. 1a, the sensor 20 also includes an array of pixels 22. The components of FIG. 1a, including the array of pixels 22, are not drawn to scale relative to the outline of the sensor 20. Each pixel produces an electric signal in response to light (from the scintillator) or x-ray radiation impinged upon it. In one embodiment, the sensor 20 includes one or more "on-board" analog-to-digital converters to covert analog signals generated by the pixels to digital signals. These signals are provided to a processor 23 (such as a programmable, electronic microprocessor, field programmable gate array, erasable programmable logic device(s), or similar device(s)). In the embodiment shown, the processor 23 is connected to memory 24 (ROM and RAM) and an input-output interface 25. The sensor 20 also includes one or more electronic circuits for power supply, driving the array of pixels, and driving the output (e.g., circuits located in the I/O interface 25). In some embodiments, the I/O interface 25 is a universal serial bus ("USB") interface.

In some embodiments, the processor 23 controls image capture or triggering of the sensor 20. In other embodiments, the x-ray source 12 is coupled to the sensor 20, e.g., via computer 30, such that when the x-ray source 12 is activated, a command is sent (simultaneously or nearly simultaneously) to the sensor 20 to perform an image capture. Thus, it is possible to generate a burst of x-ray radiation and be assured that an image will be captured by the sensor 20 during the relatively short period of x-ray exposure either through automatic triggering or via a specific capture command sent to the intraoral sensor 20.

Referring back to FIG. 1, a wire, cable, or similar connector 27 of the sensor 20 connects the sensor 20 to a computer 30. The computer 30 includes various components, including a processor or similar electronic device 32, an input/output interface 34, and memory 36 (e.g., RAM and ROM). In some embodiments, the input/output interface 34 is a USB connection and the cable 27 is a USB cable. FIG. 1 illustrates that image data captured by the sensor 20 and processed by the computer 30 is sent to a display 38 and viewed as image 40. (Image 40 is drawn more distinctly than an x-ray image would typically appear.)

The location of the intraoral sensor 20 in the patient's mouth determines what part of the patient's anatomy can be imaged (e.g., the upper jaw versus the lower jaw or the incisors versus the molars.) An x-ray operator places (or assists the patient in placing) the intraoral sensor 20 at a desired location with the patient's mouth. Various sensor holders (including those that are used with or that include a collimator) may be used to keep the sensor 20 in the desired location until an image is created or captured. For example, some holders are designed so that the patient bites the holder with his or her teeth and maintain the position of the sensor 20 by maintaining a bite on the holder. After the sensor 20 is positioned behind the desired anatomical structure, and the x-ray field to be generated by the x-ray source 12 is aligned with the sensor 20, it is possible that the source 12 and sensor 20 will, nevertheless, become misaligned. Misalignment can be caused by the patient moving his or her head, moving the intraoral sensor 20 (by re-biting the holder, moving his or her tongue, etc.), and other causes.

Figure 2:
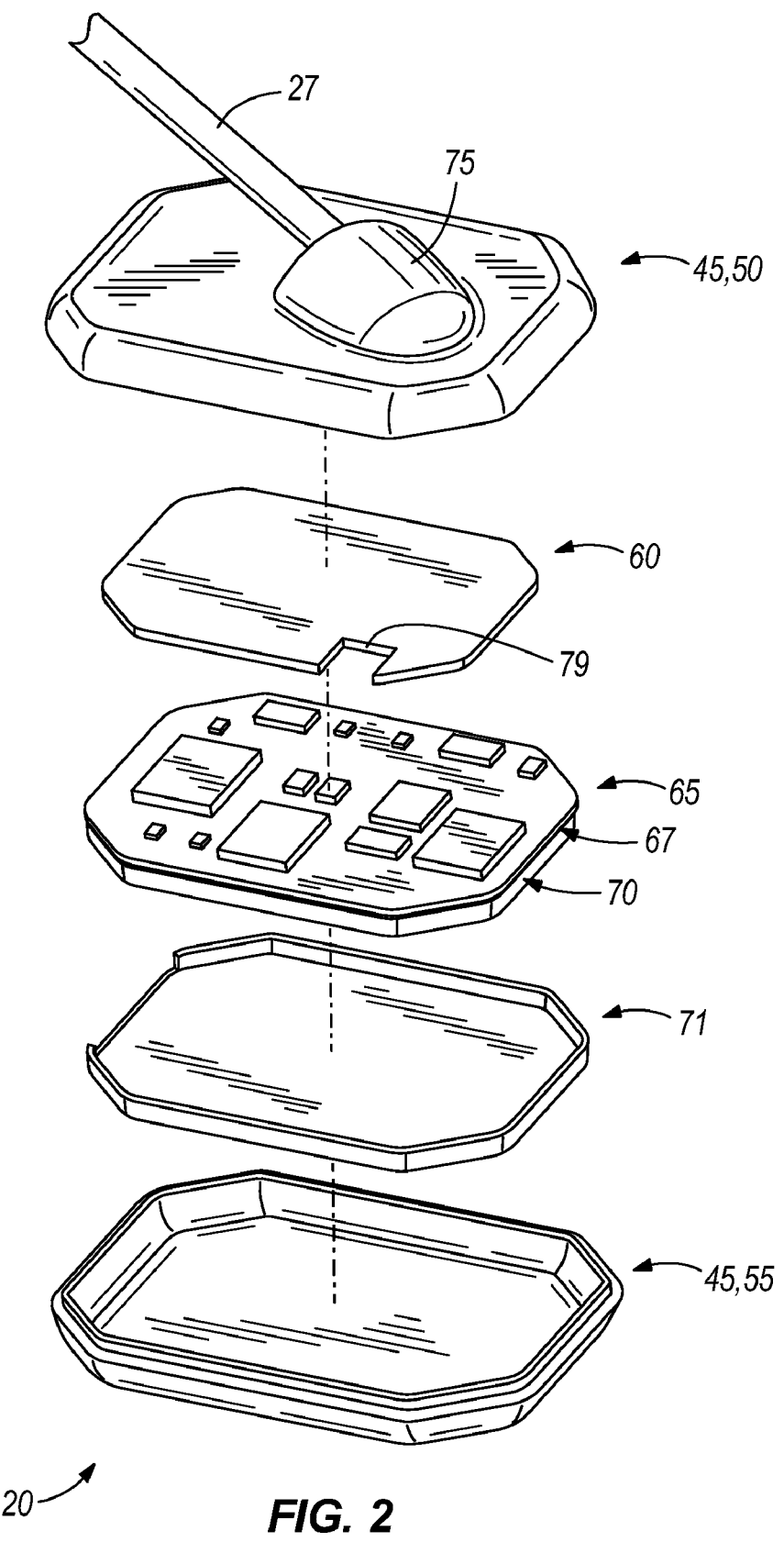
FIG. 2 depicts an exploded view of the intraoral sensor shown in FIG. 1.

FIG. 2 depicts an exploded view of the intraoral sensor 20. The sensor 20 includes a housing 45. The housing 45 has a top portion 50 and a bottom portion 55. Within the housing 45 is an insulator 60, a printed circuit board ("PCB") 65, a silicon detecting layer 67, an x-ray converter 70, and a cushioning layer 71, which protects against mechanical shocks. Some embodiments of the sensor 20 do not include the cushioning layer 71.

The top portion 50 includes a dome 75 that receives cable 27. The dome 75 has a shape that approximates an elliptical paraboloid divided in half by the surface 76 of the top portion 50 (a partial, elliptical paraboloid shape). Other dome shapes are contemplated for use in embodiments of the invention. The dome 75 includes a face with an approximately circular opening through which the cable 27 passes. The cable 27 includes connectors (e.g., wires), a portion of which pass through an opening 79 of the insulator 60 to connect to the PCB 65. In some embodiments, a ribbon or other connector passes through the opening 79 to couple the wires of cable 27 to the PCB 65. The insulator 60 provide electrical isolation between the PCB 65 and the housing 45 of the sensor 20. In some embodiments, the insulator 60 also secures the PCB 65 and x-ray converter 70 in position and protects each against mechanical shocks. Although the insulator 60 resists conducting electricity it is a conductor of heat, which assists in transferring heat away from the PCB 65.

The PCB 65, silicon detecting layer 67, and converter 70 include the components of the sensor 20 illustrated in FIG. 1a, namely the array of pixels 22, the processor 23, the memory 24, and I/O interface 25. In the embodiment depicted in FIG. 2, the array of pixels 22 includes a plurality of pixels, each pixel including a converting portion (i.e., a portion of converter 70) and a detecting portion (i.e., a portion of silicon detecting layer 67). The PCB 65 supports the silicon detecting layer 67 (e.g., a CMOS die) and converter 70, with the silicon detecting layer 67 being secured, e.g., using a glue or epoxy, to the PCB 65. The converter 70 converts x-rays received through the bottom portion 55 into light. The light travels to the silicon detecting layer 67, which converts the received light into charge. The charge is integrated at each pixel and the quantity of charge integrated represents the amount of x-rays received (although some of the integrated charge is attributable to noise and dark current). During a read-out of the array of pixels 22, the processor 23 determines the quantity of charge integrated at each pixel in the array of pixels 22. In some embodiments, the converter 70 and silicon detecting layer 67 include a fiber optic with scintillator. In some embodiments, the array of pixels 22 converts x-rays directly to charge without an intermediate step of converting x-ray to light. In such embodiments, among other possible alterations, an additional insulator (similar to insulator 60) is positioned in place of converter 70, and is used to provide electrical isolation between the housing 45 and the PCB 65 and help transfer heat away from the PCB 65.

Figure 3:
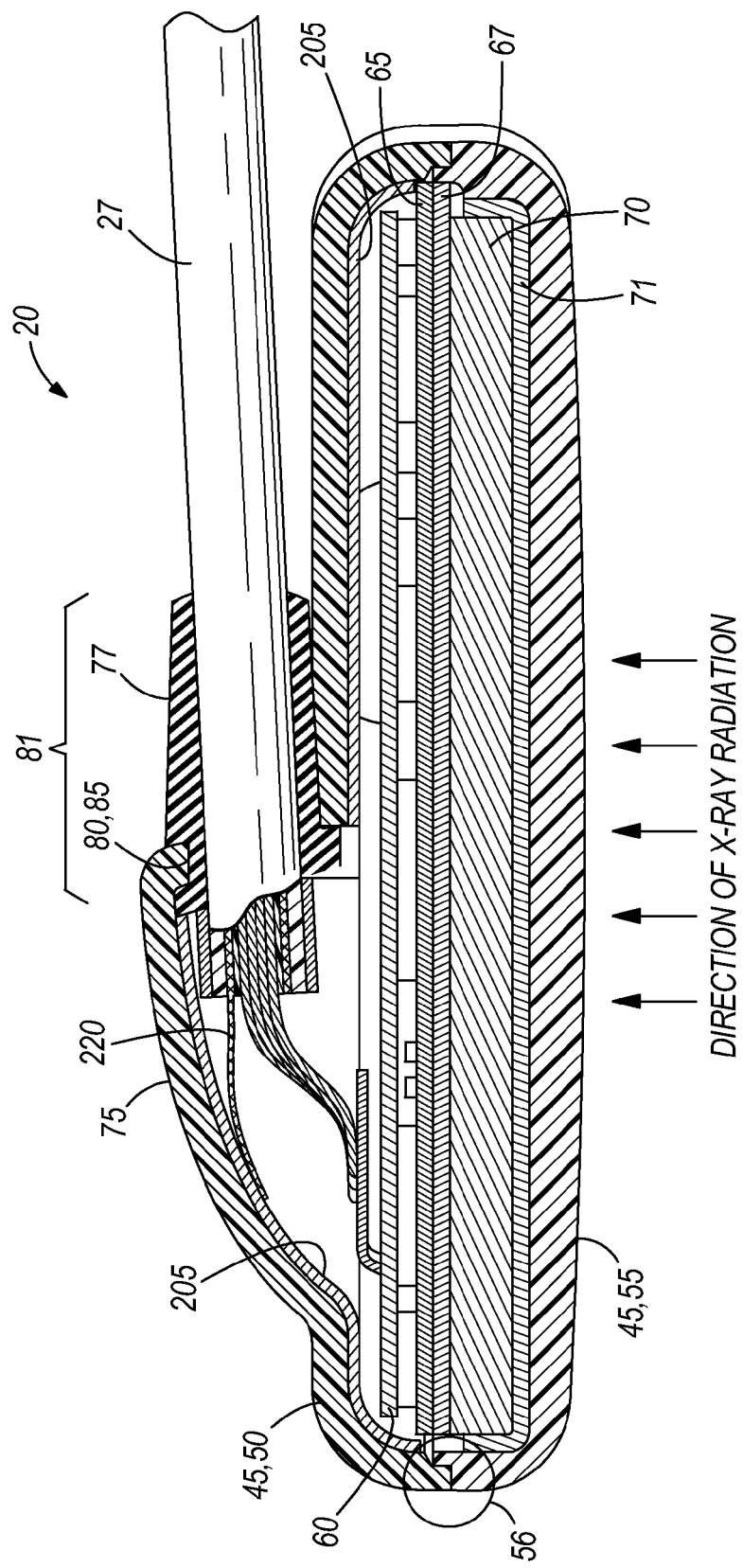
FIG. 3 depicts a cross section along line A of FIG. 4.
Figure 4:
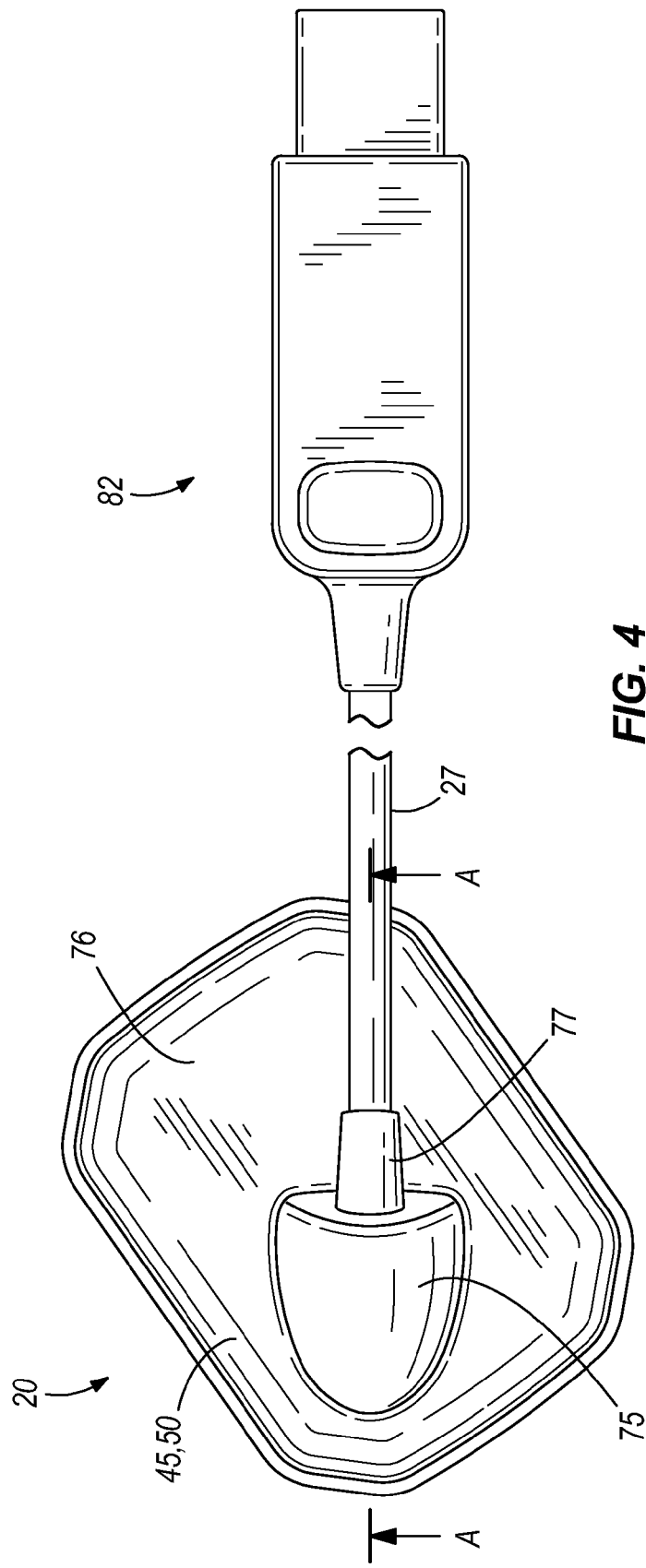
FIG. 4 depicts a top view of the intraoral sensor shown in FIG. 1 and a cable connector.

FIG. 3 depicts a cross section of the sensor 20 along line A as shown in FIG. 4. The top portion 50 is secured to the bottom portion 55 for instance, using ultrasonic welding and machining. The welding bonds the top portion 50 to the bottom portion 55, and machining smoothes the surface. Additionally, the top portion 50 and bottom portion 55 include interlocking portions 56. The converter 70, PCB 65, silicon detecting layer 67, and insulator 60 are shown within the housing 45. Also depicted is the cable 27 including stress relief portion 77. The stress relief portion 77 is secured to the cable 27, for instance, using an adhesive. Additionally, the stress relief portion 77 includes a circumferential notch 80 that matches up with ridge 85 on the dome 75. The stress relief portion 77 is secured to the dome 75 using the interlocking notch 80 and ridge 85. An adhesive may also be used to secure stress relief portion 77 to the dome 75. The stress relief portion 77 alleviates mechanical stress on the cable-to-housing coupling 81 created from twisting, pulling, and other forces on cable 27 and housing 45. Thus, the stress relief portion 77 extends the life of the cable-to-housing coupling 81, preventing or delaying malfunction of the sensor 20 caused by breaking the connection between the cable 27 and the housing 45. FIG. 4 depicts a top view of the sensor 20 and a USB connector 82 at the end of cable 27.

Figure 5A:
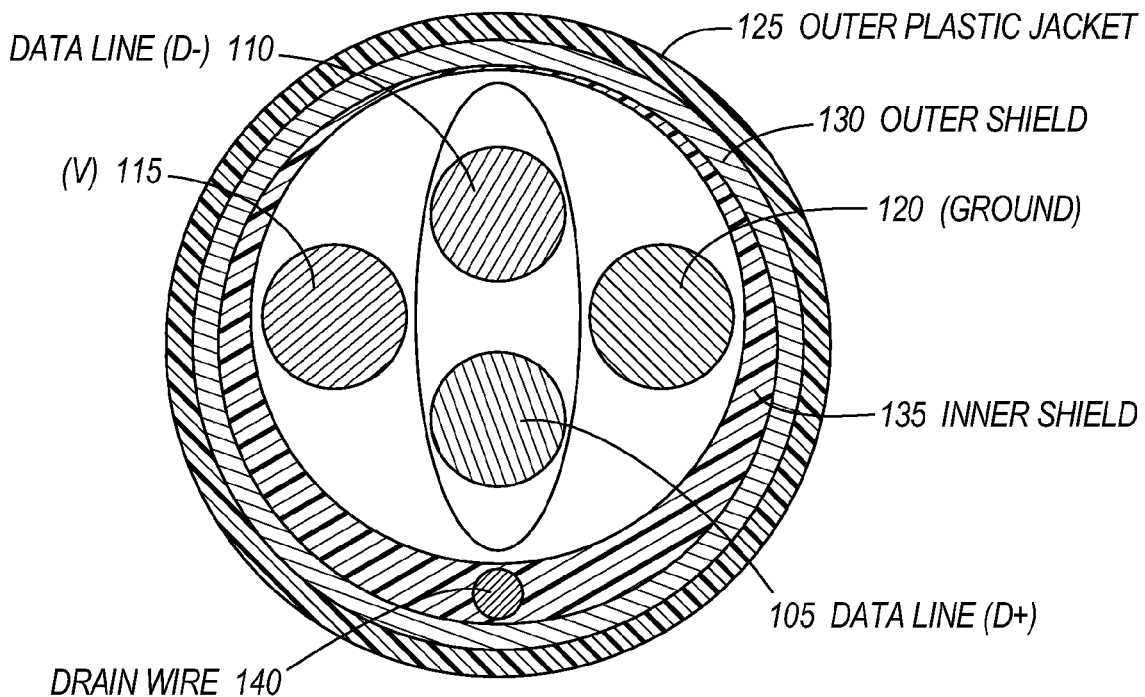
FIG. 5a depicts a cross section of a prior-art universal serial bus (USB) cable.

FIG. 5a depicts a cross section of a standard universal serial bus (USB) cable 100 capable of high speed USB version 2.0 communication. The standard USB cable 100 includes four main wires: data line 105 (D+), data line 110 (D−), power line 115, and ground line 120. Additionally, surrounding the four main wires is an isolating jacket 125, an outer shield 130 made of 65% interwoven tinned copper braid, and an inner shield 135 made of aluminum metallized polyester. The isolating jacket 125 is made of polyvinyl chloride (PVC) in some embodiments. Running lengthwise along with wire between the inner shield 135 and the outer shield 130 is a copper drain wire 140. The standard USB cable 100 is not symmetrical. Rather, the standard USB cable 100 has an internal, non-circular, oval structure, although fillers and plastic (not shown) may be used to create an external, circular shape of the cable. The external, circular shape can be approximately 4 mm in diameter.

Figure 5B:
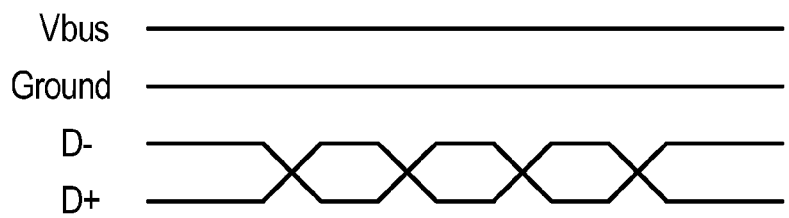
FIG. 5b depicts a wiring diagram of a prior-art universal serial bus (USB) cable.

FIG. 5b depicts a wiring diagram of the standard USB cable 100. As illustrated, the standard USB cable 100 has one twisted signaling pair including the data line 105 (D+) and data line 110 (D−). In some implementations, the power line 115 and ground line 120 are twisted (possibly to a lesser extent) or, as shown in FIG. 5b, not twisted at all.

FIG. 6a depicts a cross section of a cable 150 according to embodiments of the invention. The cable 150 includes four main wires 210 and four fillers 175a-d. The four main wires 210 include data line 155 (D+), data line 160 (D−), power line 165, and ground line 170, which provide data transmission, power transmission, and grounding, respectively. The data line 155 (D+), data line 160 (D−), power line 165, and ground line 170 each include a metal conductor encapsulated by a co-axial insulator. The four fillers 175a-d are made of plastic and are twisted along with the four main wires 210 to form a twisted quad cable. The four mains wires 210 and four fillers 175a-d are surrounded by three layers that run the length of the cable 150. The three layers include polytetrafluoroethylene ("PTFE") tape 180, a braided shield 185, and a polyurethane jacket 190. In some embodiments, other materials are used for the jacket 190 and the tape 180 (e.g., another material similar to PTFE with a low surface roughness). The braided shield 185 is made up of, for instance, tinned copper wires with 0.08 mm diameter (40 AWG). As will be discussed further below, in some embodiments, the braided shield 185 is a heat conductor. In some embodiments, the polyurethane jacket 190 is approximately 0.432 mm thick. The total diameter of the cable 150 is less than 3.0 mm. In some embodiments, additional or fewer layers surround the four main wires 210 and fillers 175a-d used within cable 27.

The wiring diagram of FIG. 6b illustrates the main wires 210 and fillers 175a-d twisted together to form a single bundle 195. Although not shown in FIG. 6b, the ("PTFE") tape 180, a braided shield 185, and a polyurethane jacket 190 encapsulate the single bundle 195 as shown in FIG. 6a. The twisted quad cable is symmetrical about center line 197, as shown in FIG. 6a. The symmetrical characteristic of the cable 150 provides increased strength and resistance to mechanical stress with a lower outside diameter, relative to the standard USB cable. That is, the cable 150 is less susceptible to damage from twisting, pulling, and other forces on the cable 150, despite the reduced diameter of the cable 150. In particular, the cable 150 is less susceptible to damage due to rotational mechanical stress, which is often present during use of an intraoral sensor cable.

Figure 7:
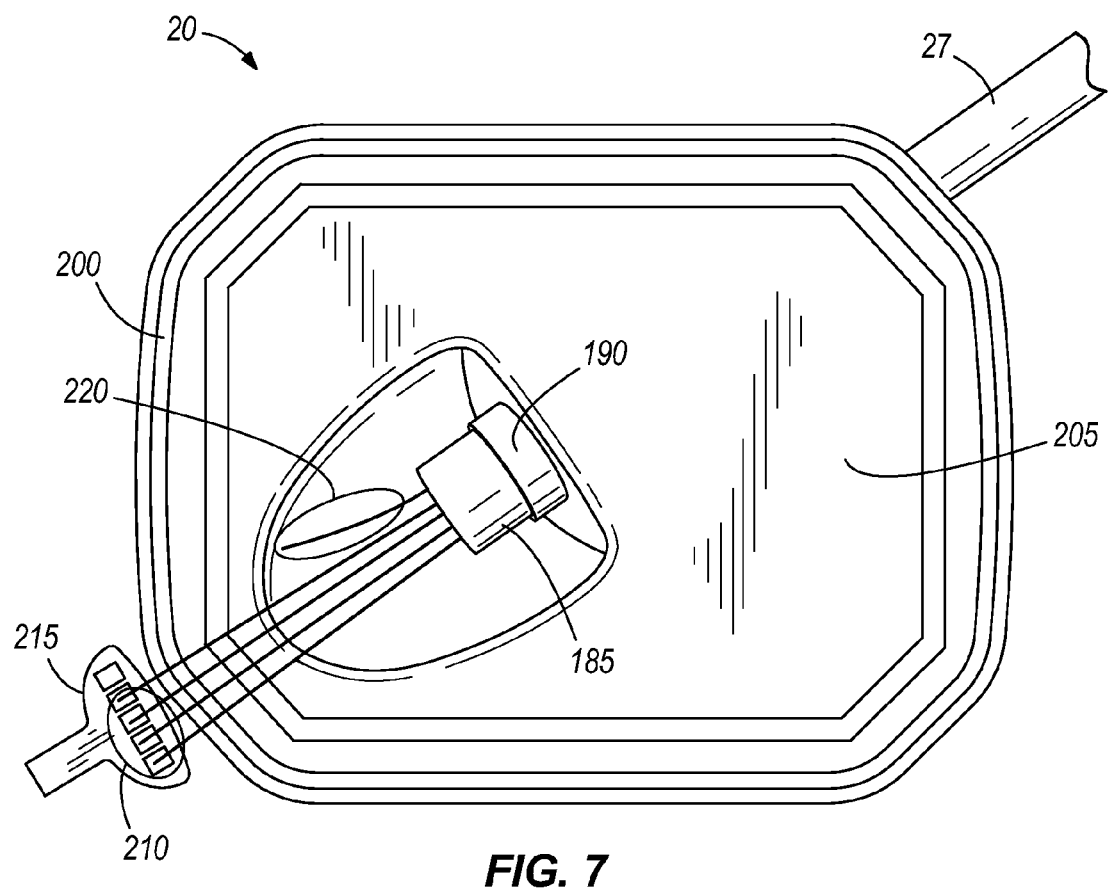
FIG. 7 depicts the underside of the top cover of the intraoral sensor of FIG. 1.

FIG. 7 depicts the inside 200 of the top portion 50. The inside 200 includes a metallization layer 205. The cable 27 is shown inserted into the dome 75. The four main wires 210 (i.e., the data line 155 (D+), data line 160 (D−), power line 165, and ground line 170) are attached to a PCB connector 215, which is connected to the PCB 65. In some embodiments, the four main wires 210 are coupled or soldered directly to the PCB 65. The braided shield 185 is coupled to the metallization layer 205 via a heat conducting wire 220. The heat conducting wire 220 is coupled to the braided shield 185 and metallization layer 205 by, for instance, soldering.

As the PCB 65 generates heat while in operation, a substantial portion of the generated heat is transferred through the insulator 60 to the metallization layer 205. The portion of generated heat is then transferred to the braided shield 185 via the heat conducting wire 220. The level of thermal resistance may vary by application. For instance, the more heat the PCB 65 generates in a particular embodiment, the lower the thermal resistances are of the materials chosen for the metallization layer 205, heat conducting wire 220, and insulator 60. In general, however, the insulator 60 and heat conducting wire 220 have a thermal resistance that is lower than the thermal resistance of air (which is approximately 1/0.025 W/(mK) at 20 degrees Celsius). Additionally, the metallization layer 205 has a thermal resistance that is less than the thermal resistance of the top portion 50 of the housing 45 and less than the thermal resistance of air. Thus, the sensor 20 provides improved heat transfer away from the sensor 20 along the cable 27.

Although not shown, in some embodiments the inside of the bottom portion 55 also includes a metallization layer, which is similar to the metallization layer 205 in form and function. The bottom metallization layer is coupled to the braided shield 185 as well. In some embodiments, the coupling is provided by an additional heat conductor connection between the bottom metallization layer and either the braided shield 185 or the metallization layer 205. In other embodiments, the coupling is provided by direct contact between the bottom metallization layer and the metallization layer 205.

Thus, the invention provides, among other things, an intraoral sensor with a cable providing greater resistance to mechanical stress. Additionally, the invention provides an intraoral sensor with improved heat transfer. Various features and advantages of the invention are set forth in the following claims.

What is claimed is:

1. An intraoral x-ray sensor comprising:
a sensor housing having a top portion and a bottom portion;
a twisted-quad universal serial bus (USB) cable coupled to the top portion, the twisted-quad USB cable including an outer sheath;
a first data line, a second data line, a ground line, and a power line positioned within the outer sheath and twisted together to form a single bundle; and
circuitry within the sensor housing that converts x-rays received through the bottom portion into x-ray data and outputs the x-ray data along the twisted-quad USB cable, and
wherein the outer sheath includes a shield and is coupled via a heat-conducting path to a metallic layer substantially covering an inner surface of the top portion, and
wherein the heat-conducting path has a thermal resistance that is less than the thermal resistance of air.

2. The sensor of claim 1, wherein four fillers are also twisted within the single bundle.

3. The sensor of claim 2, wherein the four fillers are made up of a plastic, electrically insulating material.

4. The sensor of claim 2, wherein the first data line, the second data line, the ground line, the power line, and the four fillers are symmetrically organized about a centerline of the twisted-quad USB cable.

5. The sensor of claim 2, wherein the four fillers include a first filler, a second filler, a third filler, and a fourth filler, and wherein
the first filler abuts the ground line and the first data line,
the second filler abuts the ground line and the second data line,
the third filler abuts the power line and the first data line, and
the fourth filler abuts the power line and the second data line.

6. The sensor of claim 1, further comprising an isolation layer within the sensor housing, wherein the isolation layer is between the circuitry and the top portion and wherein the isolation layer is electrically insulating and heat conducting.

7. The sensor of claim 6, wherein the isolation layer is coupled to one of the metallic layer and the braided shield via one of a second heat-conducting wire and direct contact to provide heat transfer from within the sensor housing to the twisted-quad USB cable.

8. The sensor of claim 1, wherein the outer sheath further comprises a jacket layer outside of the braided shield and a tape layer inside of the braided shield.

9. The sensor of claim 1, wherein the twisted-quad USB cable has a diameter of less than 3.0 millimeters.

10. An intraoral x-ray sensor comprising:
a housing including a top portion and a bottom portion, the top portion having a first inner surface and a first thermal resistance, wherein the first inner surface is substantially covered by a metallic layer with a second thermal resistance that is lower than the first thermal resistance;
circuitry within the housing that converts x-rays received through the bottom portion into x-ray data and outputs the x-ray data along a data cable, and
wherein the data cable includes wires within a metallic shield, and
wherein the metallic shield is coupled to the metallic layer by a thermally conductive path, wherein the thermally conductive path has a thermal resistance that is less than the thermal resistance of air.

11. The sensor of claim 10, wherein the bottom portion includes a second inner surface substantially covered by a second metallic layer, wherein the second metallic layer is coupled to the metallic layer either directly or via another thermally conductive path.

12. The sensor of claim 10, wherein the circuitry is contained on a printed circuit board (PCB), and wherein the PCB is isolated from the metallic layer by an isolation layer.

13. The sensor of claim 12, wherein the isolation layer is thermally conductive and electrically insulating.

14. The sensor of claim 12, wherein the circuitry includes an array of pixels on a first side of the PCB and, on a second side of the PCB, a processor and an input/output module.

15. The sensor of claim 14, wherein the sensor includes x-ray attenuation components between the second side and a surface of the bottom portion through which x-rays are received, and wherein the x-ray attenuation components include: a lead layer, a fiber optic scintillating layer, and copper planes.

16. The sensor of claim 12, wherein the isolation layer includes an opening through which the circuitry and the wires are connected.

17. The sensor of claim 10, wherein the top portion includes a dome having a partial, elliptical paraboloid shape and including a face with a circular opening, wherein the circular opening receives the data cable.

18. The sensor of claim 10, wherein the data cable has a diameter of less than 3.0 millimeters.

* * * * *